(12) United States Patent
Locke et al.

(10) Patent No.: US 11,887,304 B2
(45) Date of Patent: *Jan. 30, 2024

(54) SYSTEMS AND METHODS TO PROCESS ELECTRONIC IMAGES TO PRODUCE A TISSUE MAP VISUALIZATION

(71) Applicant: PAIGE.AI, Inc., New York, NY (US)

(72) Inventors: Jason Locke, Westport, CT (US); Jillian Sue, New York, NY (US); Christopher Kanan, Pittsford, NY (US); Sese Ih, Brooklyn, NY (US)

(73) Assignee: Paige.AI, Inc., New York, NY (US)

( * ) Notice: Subject to any disclaimer, the term of this patent is extended or adjusted under 35 U.S.C. 154(b) by 112 days.

This patent is subject to a terminal disclaimer.

(21) Appl. No.: 17/655,524

(22) Filed: Mar. 18, 2022

(65) Prior Publication Data

US 2022/0207735 A1 Jun. 30, 2022

Related U.S. Application Data

(63) Continuation of application No. 17/350,328, filed on Jun. 17, 2021, now Pat. No. 11,315,249.

(Continued)

(51) Int. Cl.
G06K 9/00 (2022.01)
A61B 6/00 (2006.01)
G06T 7/00 (2017.01)
G16H 70/60 (2018.01)
G16H 10/40 (2018.01)
G16H 30/40 (2018.01)
(Continued)

(52) U.S. Cl.
CPC ............ *G06T 7/0012* (2013.01); *G06N 20/00* (2019.01); *G06T 3/40* (2013.01); *G06T 11/60* (2013.01); *G16H 10/40* (2018.01); *G16H 30/40* (2018.01); *G16H 70/60* (2018.01); G06T 2207/20081 (2013.01); G06T 2207/30024 (2013.01)

(58) Field of Classification Search
CPC . A61B 6/00; A61B 35/12; G06K 9/00; G06N 3/0454
USPC ....... 382/100, 103, 128–134, 151, 157, 162, 382/172–173, 181, 189, 219, 224, 254, 382/286–291, 305, 321; 378/4, 21, 89, 378/18
See application file for complete search history.

(56) References Cited

U.S. PATENT DOCUMENTS 10,664,999 B2 * 5/2020 Gupta .................... G06N 3/045
2017/0098310 A1 * 4/2017 Chefd'Hotel ............. G06T 7/12
(Continued)

FOREIGN PATENT DOCUMENTS

WO 2018065434 4/2018

*Primary Examiner* — Seyed H Azarian
(74) *Attorney, Agent, or Firm* — Bookoff McAndrews, PLLC

(57) ABSTRACT

Systems and methods are disclosed for analyzing an image of a slide corresponding to a specimen, the method including receiving at least one digitized image of a pathology specimen; determining, using the digitized image at an artificial intelligence (AI) system, at least one salient feature, the at least one salient comprising a biomarker, cancer, cancer grade, parasite, toxicity, inflammation, and/or cancer subtype; determining, at the AI system, a salient region overlay for the digitized image, wherein the AI system indicates a value for each pixel; and suppressing, based on the value for each pixel, one or more non-salient regions of the digitized image.

20 Claims, 8 Drawing Sheets

Related U.S. Application Data

(60) Provisional application No. 63/041,778, filed on Jun. 19, 2020.

(51) Int. Cl.
*G06N 20/00* (2019.01)
*G06T 3/40* (2006.01)
*G06T 11/60* (2006.01)

(56) References Cited

U.S. PATENT DOCUMENTS

| | | | |
|---|---|---|---|
| 2017/0243051 A1* | 8/2017 | Chukka | G06V 10/809 |
| 2018/0286043 A1 | 10/2018 | Barnes et al. | |
| 2021/0027462 A1* | 1/2021 | Bredno | G06V 20/695 |
| 2021/0090694 A1* | 3/2021 | Colley | G16H 50/70 |
| 2021/0256690 A1* | 8/2021 | Yip | G06V 10/82 |

* cited by examiner

US 11,887,304 B2

SYSTEMS AND METHODS TO PROCESS ELECTRONIC IMAGES TO PRODUCE A TISSUE MAP VISUALIZATION

RELATED APPLICATION(S)

This application is a continuation of U.S. Non-provisional application Ser. No. 17/350,328 filed Jun. 17, 2021, which claims priority to U.S. Provisional Application No. 63/041,778, filed Jun. 19, 2020, the entire disclosures disclosure of which are hereby incorporated herein by reference in their entireties its entircty.

FIELD OF THE DISCLOSURE

Various embodiments of the present disclosure pertain generally to image-based tissue visualization and related image processing methods. More specifically, particular embodiments of the present disclosure relate to systems and methods for tissue visualization based on processing images of tissue specimens.

BACKGROUND

Pathology is a highly visual discipline that requires identification and specialized interpretation of morphological and histological patterns. Whole slide images of pathology specimens consist of hundreds of thousands of pixels that a pathologist must review. To help them, artificial intelligence (AI) systems may be created that show heatmap overlays to indicate salient image regions, e.g., a tumor, to pathologists. However, the heatmap overlay may obscure the tissue and hinder the ability of the pathologist to study the region.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for analyzing an image of a slide corresponding to a specimen.

A method for analyzing an image of a slide corresponding to a specimen, the method comprising: receiving at least one digitized image of a pathology specimen; determining, using the digitized image at an AI system, at least one salient feature, the at least one salient feature comprising a biomarker, cancer, cancer grade, parasite, toxicity, inflammation, and/or cancer sub-type; determining, at the AI system, a salient region overlay for the digitized image, wherein the AI system indicates a value for each pixel; and suppressing, based on the value for each pixel, one or more non-salient regions of the digitized image.

A system for analyzing an image of a slide corresponding to a specimen includes a memory storing instructions; and at least one processor executing the instructions to perform a process including receiving at least one digitized image of a pathology specimen; determining, using the digitized image at an AI system, at least one salient feature, the at least one salient feature comprising a biomarker, cancer, cancer grade, parasite, toxicity, inflammation, and/or cancer sub-type; determining, at the AI system, a salient region overlay for the digitized image, wherein the AI system indicates a value for each pixel; and suppressing, based on the value for each pixel, one or more non-salient regions of the digitized image.

A non-transitory computer-readable medium storing instructions that, when executed by a processor, cause the processor to perform a method for analyzing an image of a slide corresponding to a specimen, the method including receiving at least one digitized image of a pathology specimen; determining, using the digitized image at an AI system, at least one salient feature, the at least one salient feature comprising a biomarker, cancer, cancer grade, parasite, toxicity, inflammation, and/or cancer sub-type; determining, at the AI system, a salient region overlay for the digitized image, wherein the AI system indicates a value for each pixel; and suppressing, based on the value for each pixel, one or more non-salient regions of the digitized image.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1:
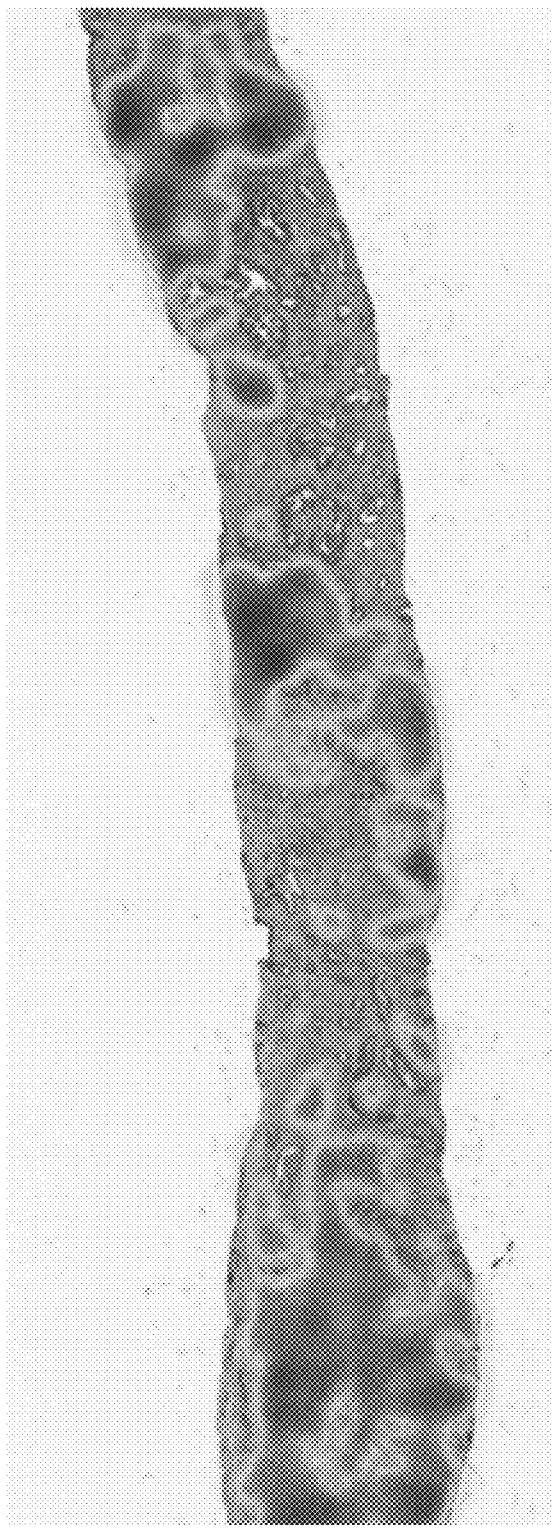
FIG. 1 is an example heatmap that indicates a presence of disease in a biopsy.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

As AI becomes more and more integrated with a pathologist's diagnostic and research workflows, the interpretability of AI technology results and the user experience while working with AI are critical to the pathologist's ability to effectively leverage the technology. In one technique, AI may be used as a post-processing mechanism to overlay prediction visualizations on an image. However, this may impede a pathologist's access and understanding of the results.

When pathologists recognize areas of interest (e.g., a tumor, interesting morphological finding, and/or something that requires consultation or review, etc.), they may draw a border around the region, for example directly on the glass slide with a marker. AI-based image analysis may be used to overlay a heatmap on the digitized pathology image. In one technique, insignificant areas are not given overlays and significant ones are. The overlays may be gradients that represent a probability map generated by the algorithm.

However, using the above methods, there may be an obtrusive overlay on relevant areas. Because the heatmap may be displayed on top of the digital image, pathologists may be forced to repeatedly toggle on and off the overlay so that they may compare what the AI pointed out to the actual tissue that lies underneath.

An AI system may generate a score and/or probability for each pixel analyzed relative to the target question (e.g., "Is there cancer?", "Is this a high-grade cancer?", etc.), and these scores may create a heatmap (e.g., FIG. 1). This may be a helpful visualization for some use cases, but for a pathologist it may be detrimental to the process of rendering a final interpretation. In fact, it may confuse the pathologist as he or she tries to determine meaning in colors of the heatmap in relation to the morphology of the tissue. For example, the AI might predict a first region of a prostate needle biopsy to be more likely Gleason Grade 3 than a second region of Gleason Grade 3 (e.g., the heatmap may depict this). However, it might not be helpful to a pathologist to know that one is predicted more likely to be Gleason Grade 3 than the other, since the pathologist makes a final determination.

FIG. 1 is an example heatmap that indicates the presence of cancer or other disease in a biopsy (e.g., prostate needle core biopsy). As illustrated in FIG. 1, an area of interest 1 has a tissue 10 with a heatmap 11. The heatmap 11 may obscure the tissue 10 and imply potentially misleading diagnostic relevance to different colors. Additionally, binary bitmaps may be used to mark pixels predicted to have a certain score (e.g., a probability) that is above a pre-specified threshold to indicate salient regions.

The present disclosure enables pathologists to focus their attention on multiple salient image regions, without an obtrusive overlay over these areas of interest. This type of visualization optimizes a pathologist's digital pathology workflow by allowing them to more easily identify, interpret, and engage with AI results.

The present disclosure provides a tissue visualization that does not obscure the regions on the slide that are identified to be significant for the pathologist to review. As a result, the interpretation and workflow are more efficient (e.g., no need to toggle on and off the output), resulting in a faster and more accurate diagnosis. In addition, the output is easier for a pathologist to interpret.

The present disclosure may use AI technology to detect features of interest (e.g., biomarkers, cancer, cancer grade, parasites, toxicity, inflammation, cancer sub-types, etc.) that may be necessary for pathological assessment and treatment decisions. The AI may produce a salient region overlay, and may transform the salient region overlay into a visualization that suppresses irrelevant image regions, or any image regions determined to not have diagnostic value beyond a predetermined threshold.

Significant regions on a whole slide image may be displayed and highlighted to users (e.g., pathologists), requiring minimal visual and usability overhead, in order to help them complete a specific task in the diagnostic process (e.g., cancer detection, grading, etc.). One or more embodiments may include providing a tissue visualization to a user within a clinical workflow at a hospital, lab, medical center, etc., as at least one of a web application (e.g., cloud-based and/or on-premises), a mobile application, an interactive report, a static report, and/or a dashboard.

To improve usability and/or efficiency, identified area(s) may be organized into a report with overview information. Further, an interactive review/edit may be provided to a user during review of the digitized image. Multiple features may be visualized on a single whole slide image.

The technical workflow according to one or more embodiments may be as follows: a digitized whole slide image may be created. Metadata may be generated and/or determined, which may be available from hospital and/or hardware databases. Image and corresponding data may be provided to an AI-based system and outputs may be generated. Some of the outputs may be fed into one or more systems that generate and/or display the visualization (e.g., one or multiple points or regions) to the user (e.g., pathologist). The analysis and/or display may be generated based on the query of interest (e.g., cancer, nuclear features, cell count, etc.).

Additionally, one or more embodiments of the present disclosure may be used for pre-screening (i.e., before a pathologist reviews an image) and/or after a diagnosis has been rendered (e.g., quality assurance).

Figure 2A:
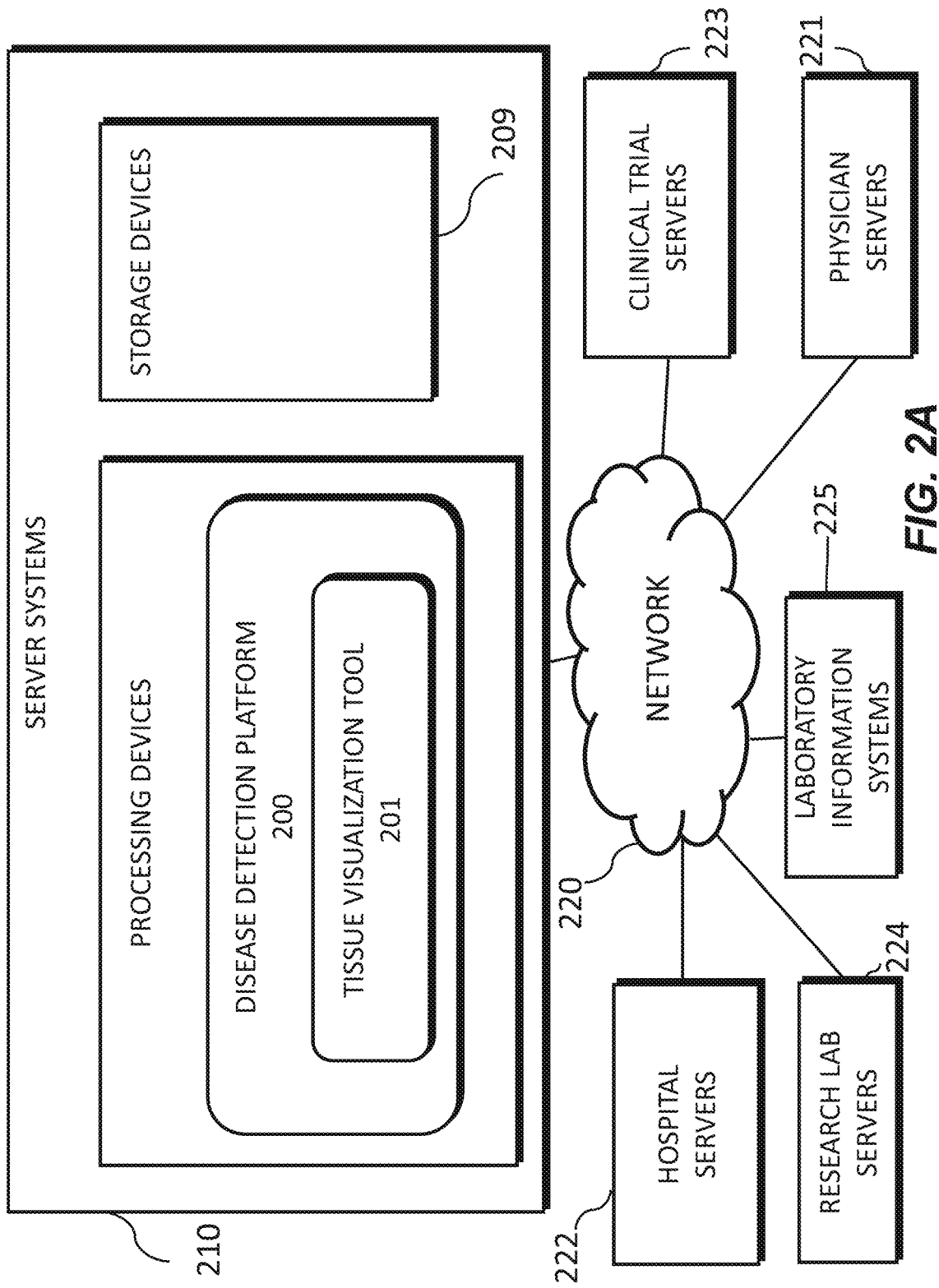
FIG. 2A illustrates an exemplary block diagram of a system and network for a tissue visualization of an image, according to an exemplary embodiment of the present disclosure.

FIG. 2A illustrates an exemplary block diagram of a system and network for a tissue visualization of an image, according to an exemplary embodiment of the present disclosure.

Specifically, FIG. 2A illustrates an electronic network 220 that may be connected to servers at hospitals, laboratories, and/or doctors' offices, etc. For example, physician servers 221, hospital servers 222, clinical trial servers 223, research lab servers 224, and/or laboratory information systems 225, etc., may each be connected to, and may communicate via, an electronic network 220, such as the Internet, through one or more computers, servers, and/or handheld mobile devices. According to an exemplary embodiment of the present application, the electronic network 220 may also be connected to server systems 210, which may include processing devices that are configured to implement a disease detection platform 200, which includes a tissue visualization tool 201 for producing a tissue visualization for digital pathology image(s), using machine learning, according to an exemplary embodiment of the present disclosure. Exemplary machine learning models may include, but are not limited to, any one or any combination of Neural Networks, Convolutional neural networks, Random Forest, Logistic Regression, and/or Nearest Neighbor.

The physician servers 221, hospital servers 222, clinical trial servers 223, research lab servers 224, and/or laboratory information systems 225 may create or otherwise obtain images of one or more patients' cytology specimen(s), oncology specimen(s), slide(s) of the cytology/oncology specimen(s), digitized images of the slide(s) of the cytology/oncology specimen(s), or any combination thereof. The physician servers 221, hospital servers 222, clinical trial servers 223, research lab servers 224, and/or laboratory information systems 225 may also obtain any combination of patient-specific information, such as age, medical history, cancer treatment history, family history, past biopsy or cytology information, etc. The physician servers 221, hospital servers 222, clinical trial servers 223, research lab servers 224, and/or laboratory information systems 225 may transmit digitized slide images and/or patient-specific information to server systems 210 over the electronic network 220. Server systems 210 may include one or more storage devices 209 for storing images and/or data received from at least one of the physician servers 221, hospital servers 222, clinical trial servers 223, research lab servers 224, and/or laboratory information systems 225. Server systems 210 may also include processing devices for processing images and/or data stored in the storage devices 209. Server systems 210 may further include one or more machine learning tool(s) or capabilities. For example, the processing devices may include a machine learning tool for a disease detection platform 200, according to one embodiment. Alternatively or in addition, the present disclosure (or portions of the system and methods of the present disclosure) may be performed on a local processing device (e.g., a laptop).

The physician servers 221, hospital servers 222, clinical trial servers 223, research lab servers 224, and/or laboratory information systems 225 refer to systems that may be used by pathologists for reviewing the images of the slides. In hospital settings, tissue type information may be stored in a laboratory information systems 225.

Figure 2B:
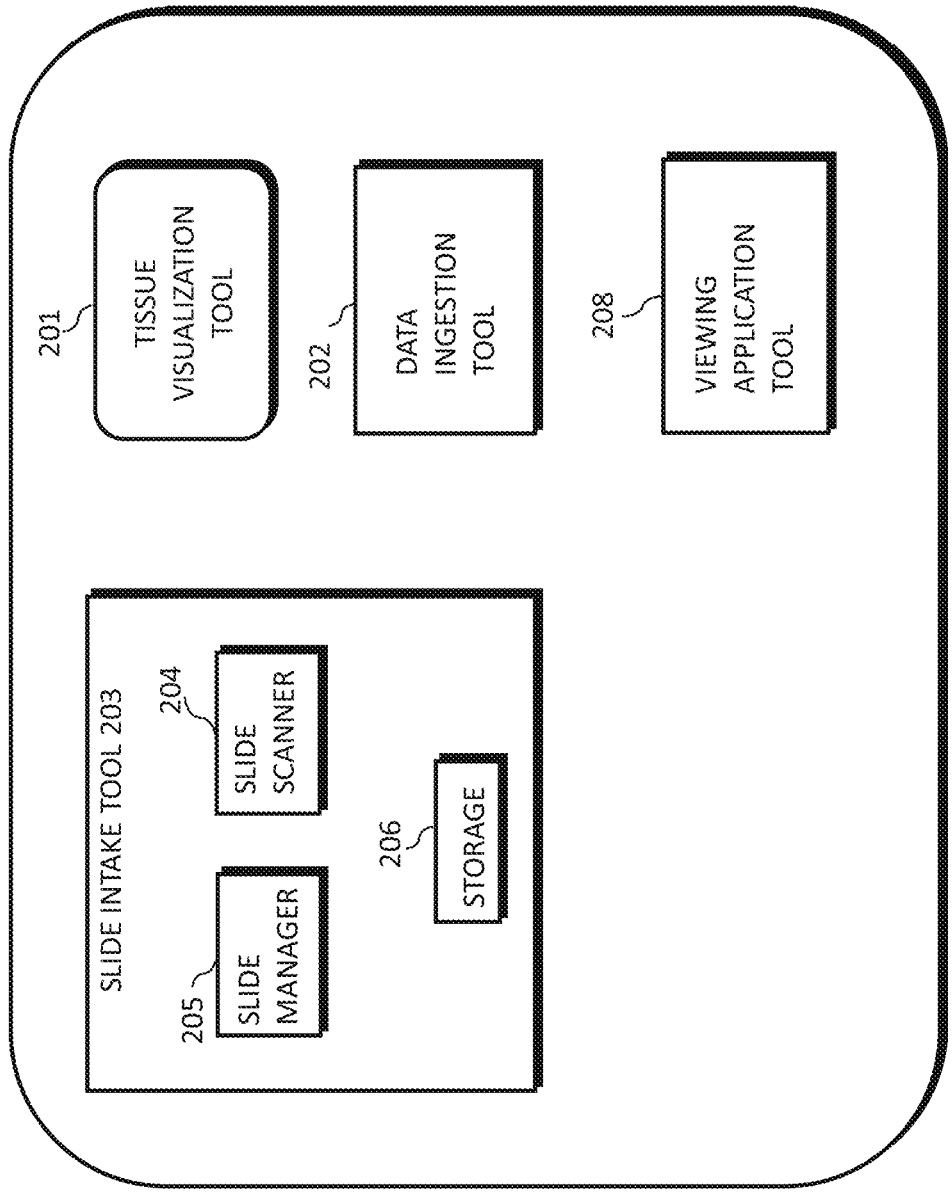
FIG. 2B illustrates an exemplary block diagram of a disease detection platform 200, according to an exemplary embodiment of the present disclosure.

FIG. 2B illustrates an exemplary block diagram of a disease detection platform 200 for producing a tissue visualization for digital pathology image(s), using machine learning.

Specifically, FIG. 2B depicts components of the disease detection platform 200, according to one embodiment. For example, the disease detection platform 200 may include a tissue visualization tool 201, a data ingestion tool 202, a slide intake tool 203, a slide scanner 204, a slide manager 205, a storage 206, and/or a viewing application tool 208.

The tissue visualization tool 201, as described below, refers to a process and system for producing a tissue visualization pertaining to digital pathology image(s), using machine learning, according to an exemplary embodiment.

The data ingestion tool 202 refers to a process and system for facilitating a transfer of the digital pathology images to the various tools, modules, components, and/or devices that are used for classifying and/or processing the digital pathology images, according to an exemplary embodiment.

The slide intake tool 203 refers to a process and system for scanning pathology images and converting them into a digital form, according to an exemplary embodiment. The slides may be scanned with slide scanner 204, and the slide manager 205 may process the images on the slides into digitized pathology images and store the digitized images in a storage, such as storage 206 and/or storage devices 209.

The viewing application tool 208 refers to a process and system for providing a user (e.g., pathologist) with specimen property or image property information pertaining to digital pathology image(s), according to an exemplary embodiment. The information may be provided through various output interfaces (e.g., a screen, a monitor, a storage device, and/or a web browser, etc.).

The tissue visualization tool 201, and each of its components, may transmit and/or receive digitized slide images and/or patient information to server systems 210, physician servers 221, hospital servers 222, clinical trial servers 223, research lab servers 224, and/or laboratory information systems 225 over an electronic network 220. Further, server systems 210 may include storage devices for storing images and/or data received from at least one of the tissue visualization tool 201, the data ingestion tool 202, the slide intake tool 203, the slide scanner 204, the slide manager 205, and/or viewing application tool 208. Server systems 210 may also include processing devices for processing images and/or data stored in the storage devices. Server systems 210 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools, and/or modules may be located on a device that may be connected to an electronic network 220, such as the Internet or a cloud service provider, through one or more computers, servers, and/or handheld mobile devices.

Figure 3:
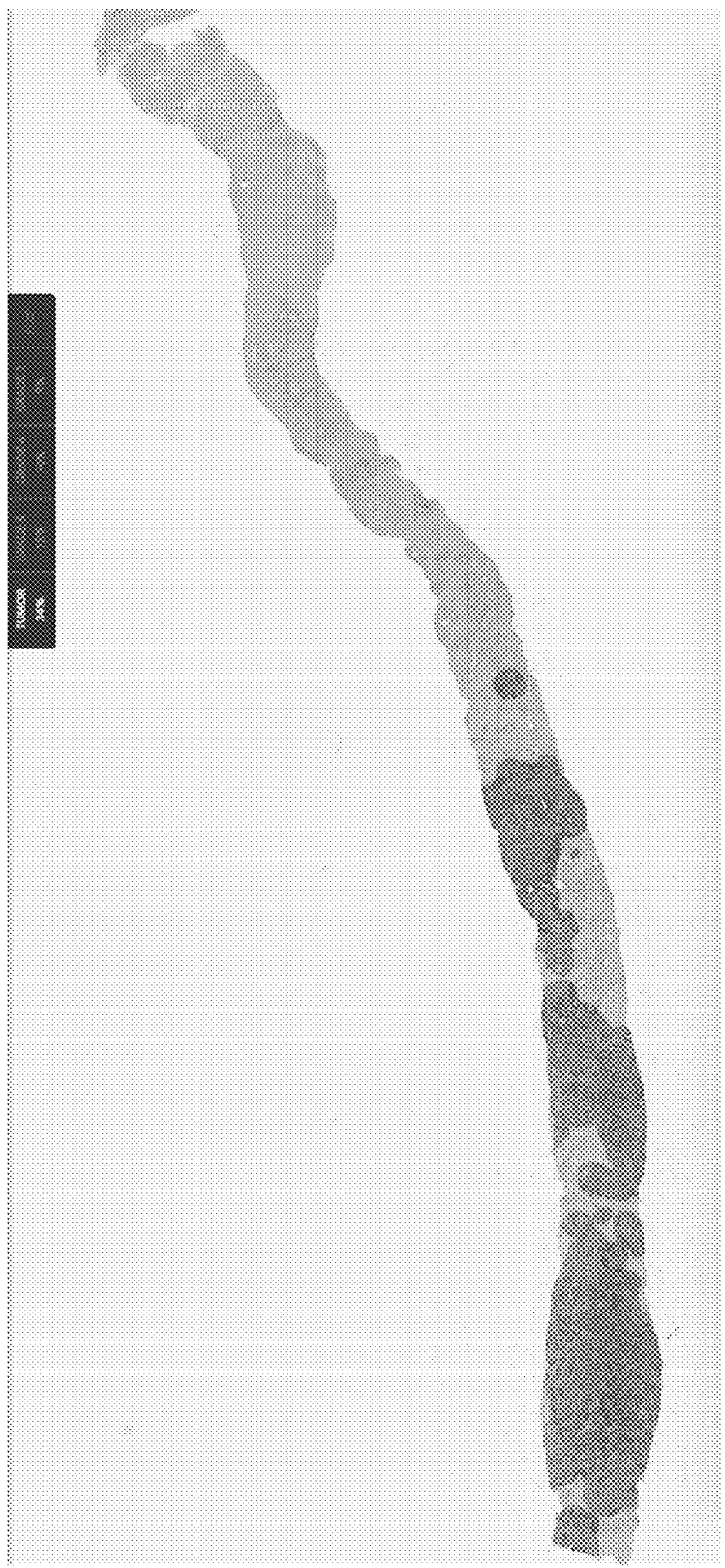
FIG. 3 illustrates an example visualization of specific regions that the AI detected as having diagnostic value, suppressing the visualization of areas with no diagnostic value, according to an exemplary embodiment of the present disclosure.

FIG. 3 illustrates an example visualization of specific regions that the AI detected as having diagnostic value, such as cancer, wherein the visualization of non-diseased regions, or other area lacking diagnostic value, is suppressed according to technique discussed herein. In the area of interest 1, tissue 10 has a non-diseased region 12 suppressed in comparison to the specific region of diagnostic value 13. A display icon 14 may also be included in the visualization.

Figure 4:
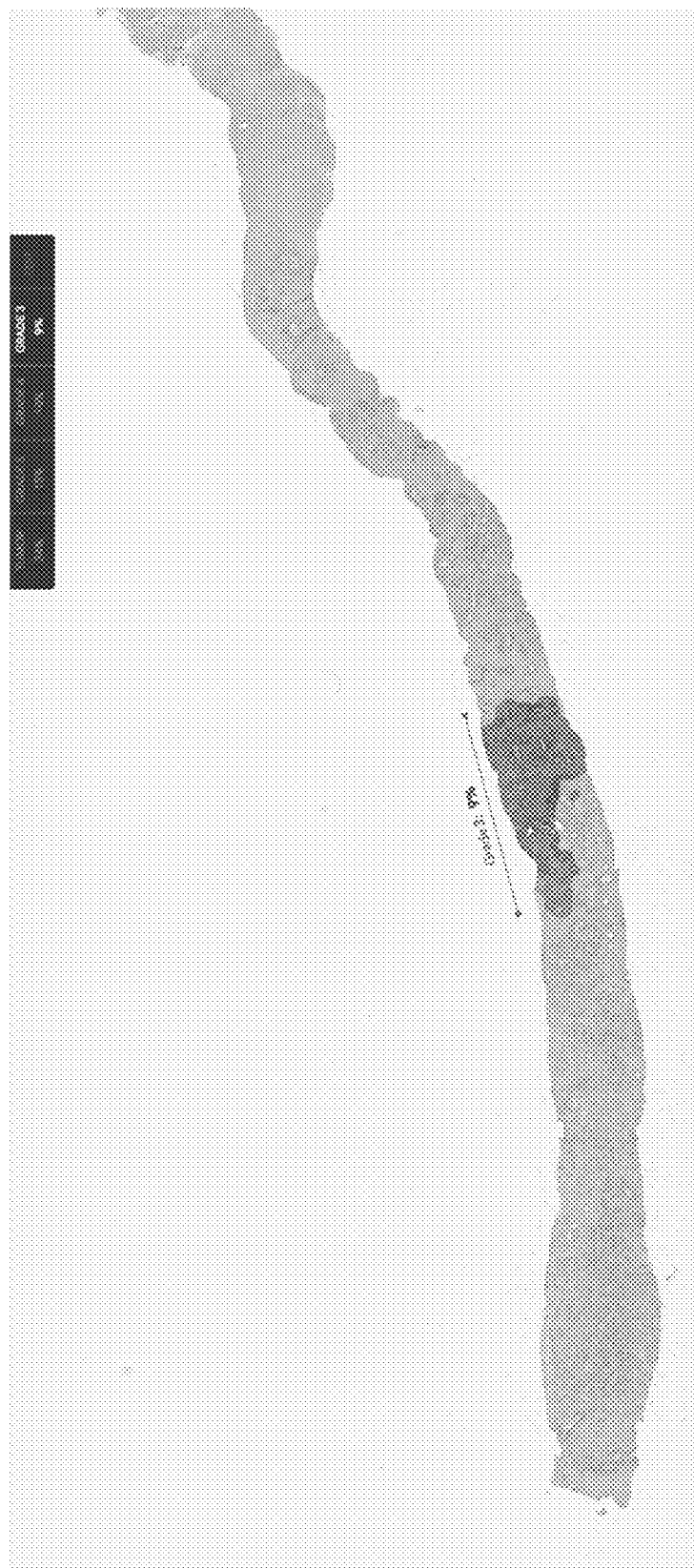
FIG. 4 illustrates an example visualization of specific regions based on a feature, according to an exemplary embodiment of the present disclosure.

FIG. 4 illustrates an example visualization of specific regions based on a feature (e.g., cancer grade), wherein the visualization of non-diseased regions, or other area lacking diagnostic value relative to the feature, is suppressed according to technique discussed herein. In the area of interest 1, tissue 10 has a non-diseased region 12 suppressed in comparison to the specific region of diagnostic value 13. A display icon 14 may also be included in the visualization.

Figure 5:
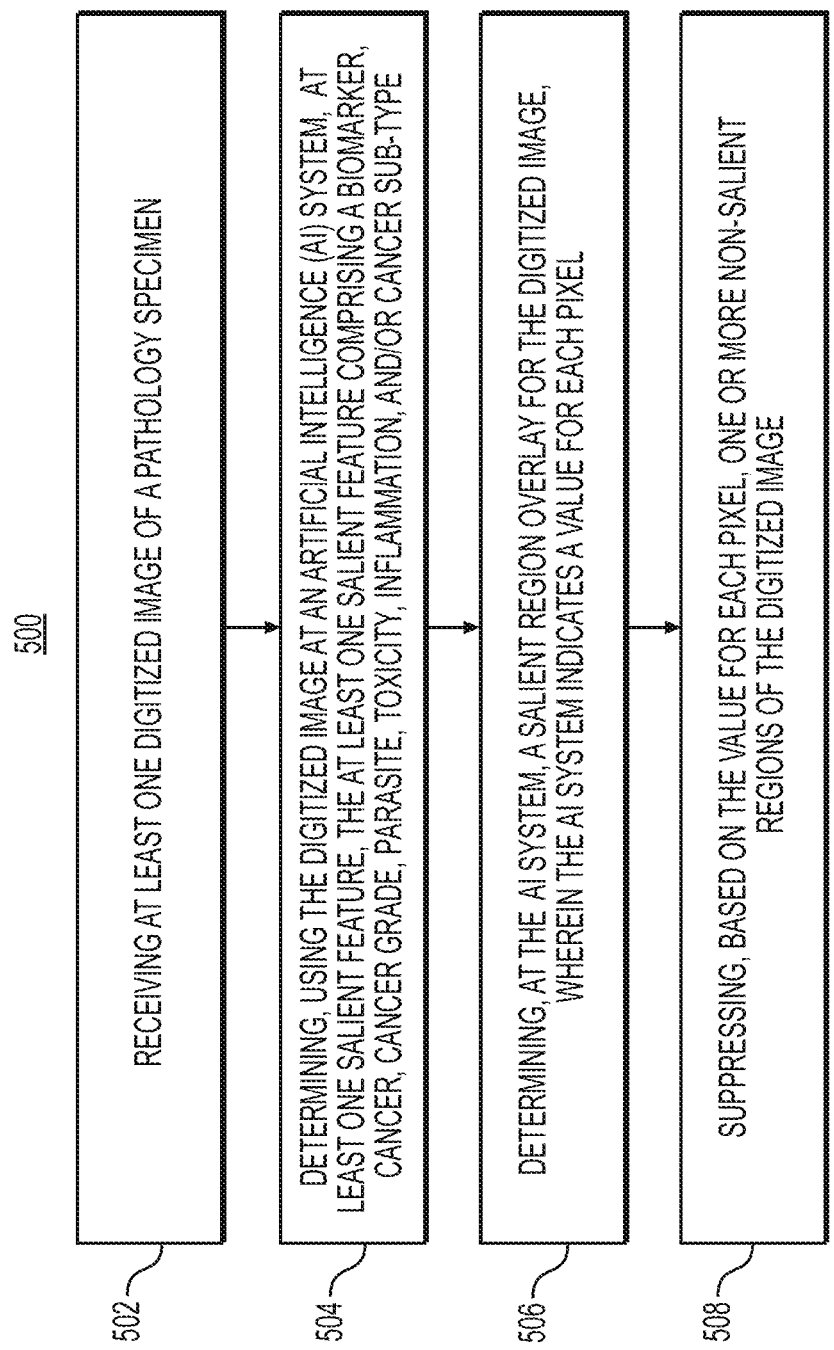
FIG. 5 is a flowchart of an exemplary method for providing a tissue visualization of a digitized pathology image, according to an exemplary embodiment of the present disclosure.

FIG. 5 is a flowchart illustrating an exemplary method for providing a tissue visualization of a digitized pathology image, according to an exemplary embodiment of the present disclosure. For example, an exemplary method 500 (e.g., steps 502 to 508) may be performed by the tissue visualization tool 201 automatically or in response to a request from a user (e.g., pathologist, patient, oncologist, etc.).

An exemplary method 500 for developing a tissue visualization tool may include one or more of the steps below. In step 502, the method may include receiving at least one digitized image of a pathology specimen (e.g., histology), which may also include related case and patient information (e.g., specimen type, case and patient ID, parts within case, gross description, etc.), and/or information from clinical system (e.g., assigned pathologist, specimens available for tests, etc.). The method may include developing a pipeline that archives processed images and/or prospective patient data. Additionally, data may be stored into a digital storage device (e.g., hard drive, network drive, cloud storage, RAM, etc.).

In step 504, the method may include determining, using the digitized image at an AI system, at least one salient feature, the at least one salient feature comprising a biomarker, cancer, cancer grade, parasite, toxicity, inflammation, and/or cancer sub-type.

In step 506, the method may include determining, at the AI system, a salient region overlay for the digitized image, wherein the AI system indicates a value for each pixel. The AI system output may be a salient region overlay M for the digital input image, which indicates a value for each pixel. The AI may represent M in a number of ways. For example M may be represented by (1) a heatmap indicating the scores or probabilities for each pixel of a salient feature being present or absent; (2) a set of super-pixels that have scores or probabilities associated with them for a feature being present or absent; (3) a binary segmentation of the tissue that indicates if each pixel has or does not have the salient feature present; and/or (4) a semantic segmentation of the image that indicates a score or probability for each pixel. Additionally, the salient region overlay may be resized to the same size as the digital image.

In step 508, the method may include suppressing, based on the value for each pixel, one or more non-salient regions of the digitized image. A salient region overlay may be processed (e.g., post-processed) and may be normalized to obtain S (e.g., normalized salient region overlay). For example, for a binary M, M may be left unmodified, i.e., S=M. As another example, using image processing techniques for binary or continuous M, the method may include (1) setting S=M; (2) applying smoothing operations to S, e.g., Gaussian or Median blur; (3) if S is not in the range of 0 to 1, normalizing S to this range, e.g., using linear contrast stretching; (4) if S has continuous values, thresholding S so that all values above a threshold are set to 1 and all values below the threshold are set to 0; and/or (5) post-processing S with morphological operators (e.g., close, erode, dilate) to improve the visualization. As another example, using segmentation for M with continuous scores or probabilities, the method may include (1) running a segmentation algorithm on M such as clustering methods (e.g., k-means), region growing methods, graph-based methods, and/or other segmentation methods; (2) assigning each segment a value based on the score/probability of the pixels that belong to it, which could be done in a many ways, e.g., taking a max score/probability of the underlying pixels, a median, a mean, and/or a generalized mean; and/or (3) to obtain S from a segmentation and calculated segment values, setting each segment with a value above a pre-determined threshold has all values to 1, and setting all values below the threshold to 0.

Figure 6A:
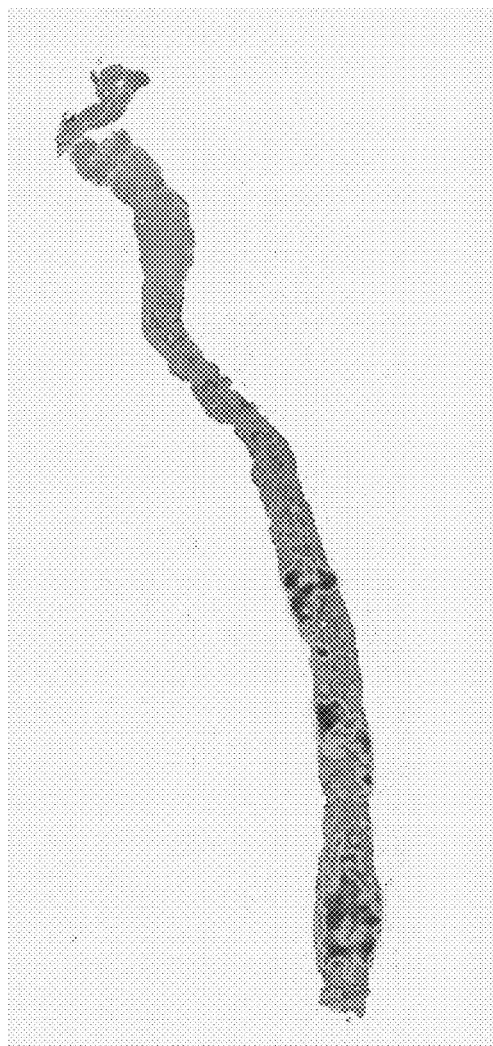
FIG. 6A is an example heatmap that indicates a presence of disease, in which a tissue for review is obscured.

FIG. 6A is an example heatmap that indicates a presence of cancer, in which a tissue is obscured. As discussed above, the heatmap may obscure tissue relevant to diagnosis by the pathologist.

Figure 6B:
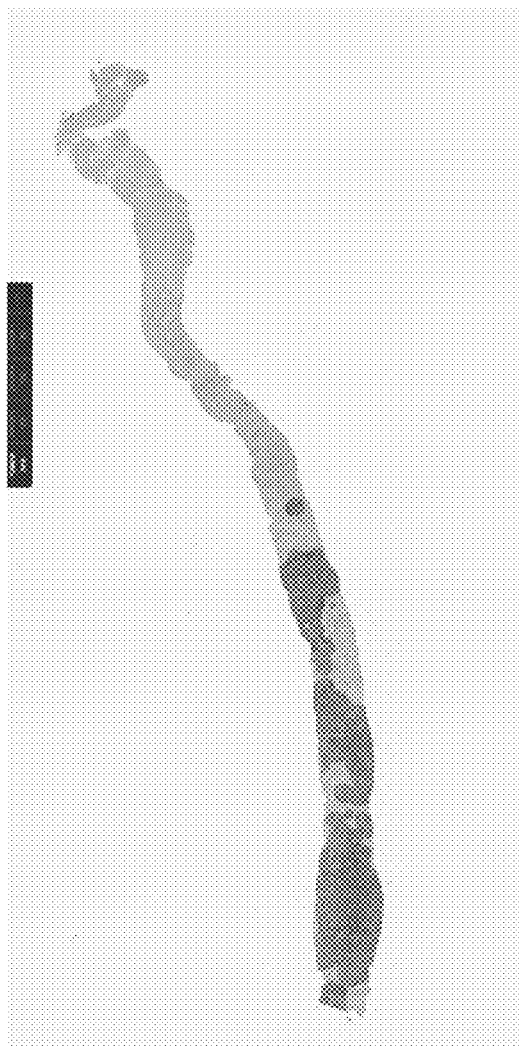
FIG. 6B is illustrates an example visualization of regions with disease, without obscuring the tissue for review, according to an exemplary embodiment of the present disclosure.

Techniques discussed in relation to FIG. 5, and elsewhere herein, may be used to generate the visualization of FIG. 6B. Regions with cancer or other diagnosable problems may be easily seen in the visualization, without any obscuring of the tissue for review. Regions not relevant to diagnosis, such as non-salient regions, may be obscured or otherwise suppressed.

When the visualization and/or report is generated, a user (e.g., pathologist, oncologist, patient, etc.) may be made aware that results are available, via a notification. The user may be provided an option to review visualization and/or report. Alternatively, the visualization and report may be automatically provided. If the user opts to view the visualization, or if the system is set to show it automatically, then the tissue map may use S to suppress pixels z in which that pixel in S, i.e., S (z) has a value of 0, which indicates that the AI does not interpret it to be diagnostic for the clinical feature of interest (non-salient). This suppression may be done by at least one of "blacking out" these pixels, making them partially transparent, changing their brightness, and/or other methods of visual differentiation.

The user may customize what the tissue visualization shows based on the target output (target outputs may include: regions marked by the user or other users, morphological features, areas not viewed by anyone based on tracking software, etc.). The tissue map may be utilized to visualize multiple M's (salient region overlays) on a single slide. If one slide has multiple M's, then the user may select which M (e.g., one or multiple) to display at one time. The user may add or delete areas within S based on their expert assessment. For example, the user may modify the visualization (e.g., include more tissue) using their mouse or input device, and any corresponding details will be adjusted as well (e.g., as more tumor is identified, the displayed value for quantification of tumor will adjust accordingly). Any changes may be reset so that the user may return to the original prediction and visualization.

The user's field of view may be moved to focus upon each identified region of interest (e.g., a region of interest may be any region identified on the tissue map by AI or by the user as an area that requires further investigation) in order of priority, class, and/or other preferential orders. The outputs and/or visualized regions may be logged as part of the case history within the clinical reporting system.

Exemplary Cancer Detection Tool: According to one embodiment, a method includes identifying tissue regions with cancer. A tissue map helps users, e.g., pathologists, more quickly identify tissue regions that have cancer or are suspicious for cancer. Using an AI that produces a salient region overlay M that indicates which tissue regions have cancer or are suspicious for cancer, a tissue visualization may be created using the steps described with respect to FIG. 5. The present disclosure provides systems and methods for modifying the tissue map, for example, target customizations, editing capabilities, field of view, and/or recording/reporting purposes. The user may customize what the tissue map shows based on definitions for the target output. For example, if the tissue visualization displays all areas detected to be cancerous, the user may customize the output so that it either considers or doesn't consider certain features in the cancerous category (e.g., some hospitals consider atypical ductal hyperplasia (ADH) as cancerous while others do not). Thus, a user from hospital A may see all cancerous areas on a breast biopsy, including ADH while a user from hospital B may see all cancerous areas on a breast biopsy, excluding ADH. The user may interact with and/or edit the visualization and/or adjust the visualization so that more tissue is visible (e.g., if they disagree with the result and think more areas are cancerous) or less tissue is visible (e.g., if they disagree with the result and think the identified areas are not cancerous). The user's field of view may be moved to focus upon each region of interest in order of priority, class, or other preferential orders. The outputs and/or visualized regions may be logged as part of a case history within the clinical reporting system.

Exemplary Cancer Grade Tool: According to one embodiment, a method includes characterizing tissue regions that have cancer using a tissue map. Exemplary systems and methods may produce a salient region overlay M that indicates which tissue regions have certain grades of cancer, and a tissue visualization may be created using the steps described with respect to FIG. 5. The user may customize what the tissue visualization shows based on definitions for the target output. For example, grading guidelines for cancer change over time. If a user wanted to see how it would have been assessed at a different time point, they could adjust accordingly. The user may interact with and/or edit the visualization. The user may adjust the visualization so that more tissue is visible (e.g., if they disagree with the result and think an area is cancer and Grade 3) or less tissue is visible (e.g., if they disagree with the result and think the identified areas are not cancerous nor Grade 3). The user's field of view may be moved to focus upon each region of interest in order of priority, class, or other preferential orders. The outputs and/or visualized regions may be logged as part of the case history within the clinical reporting system.

Exemplary Cancer Type or Pre-cancerous Lesions Tool: According to one embodiment, a method includes a tissue visualization in which multiple forms of cancer may occur (e.g., lobular and/or ductal breast cancer). Using an AI that produces a salient region overlay M that indicates which tissue regions are certain types of cancer, a tissue visualization may be created using the steps described with respect to FIG. 5. The user may customize what the tissue visualization shows based on definitions for the target output. For example, some users may prefer to see all potential pre-cancerous lesions and cancerous lesions on a slide, whereas others may only want to report a few significant pre-cancerous or atypical lesions. The user may interact with and/or edit the visualization. The user may the visualization so that more tissue is visible (e.g., if they disagree with the result and think an area is cancer and ductal) or less tissue is visible (e.g., if they disagree with the result and think the identified areas are not cancerous nor ductal). The user's field of view may be moved to focus upon each region of interest in order of priority, class, and/or other preferential orders. The outputs and/or visualized regions may be logged as part of the case history within the clinical reporting system.

Exemplary Non-Cancerous Features Tool: According to one embodiment, a method includes identifying other non-cancer features (e.g., fungus in dermatopathology samples, bacteria in colon samples, atypia in breast samples, inflammation in many tissue types, etc.). Using an AI that produces a salient region overlay M that indicates which tissue regions contain different biological features, a tissue visualization may be created using the steps described with respect to FIG. 5. The user may interact with and/or edit the visualization. The user may adjust the visualization so that more tissue is visible (e.g., if they disagree with the result and think an area is fungi) or less tissue is visible (e.g., if they disagree with the result and think the identified areas are not fungi). The user's field of view may be moved to focus upon each region of interest in order of priority, class, or other preferential orders. The outputs and/or visualized regions may be logged as part of the case history within the clinical reporting system.

Exemplary Invasion Tool: According to one embodiment, a method includes determining a presence of an invasion (e.g., microinvasion in breast cancer, muscularis propria invasion in bladder cancer, perineural invasion in prostate cancer, etc.). Using an AI that produces a salient region overlay M that indicates which tissue regions contain invasive cancer, a tissue visualization may be created using the steps described with respect to FIG. 5. The user may customize what the tissue visualization shows based on definitions for the target output. The user may interact with and/or edit the visualization. The user may adjust the visualization so that more tissue is visible (e.g., if they disagree with the result and think an area is invasive) or less tissue is visible (e.g., if they disagree with the result and think the identified areas are not invasive). The user's field of view may be moved to focus upon each region of interest in order of priority, class, and/or other preferential orders. Additionally, the outputs and/or visualized regions may be logged as part of the case history within the clinical reporting system.

Exemplary Differential Diagnoses Tool: According to one embodiment, a method includes distinguishing between differential diagnoses (e.g., dermatofibroma and leiomyoma in dermatopathology specimens). Using an AI that produces a salient region overlay M that indicates which tissue regions contain invasive cancer, a tissue visualization may be created using the steps described with respect to FIG. 5. The user may interact with and/or edit the visualization. The user may adjust the visualization so that more tissue is visible (e.g., if they disagree with the result and think an area is invasive) or less tissue is visible (e.g., if they disagree with the result and think the identified areas are not invasive). The user's field of view may be moved to focus upon each region of interest in order of priority, class, or other preferential orders. The outputs and/or visualized regions may be logged as part of the case history within the clinical reporting system. Additionally, the user may tag a tissue region with multiple user's differential diagnoses.

Exemplary Pre-Clinical Toxicity Detection Tool: According to one embodiment, a method includes salient tissue visualization used for pre-clinical drug development in which animals are given a drug and then their organs are evaluated by a pathologist to determine if there is any toxicity present. Using an AI that produces a salient region overlay M that indicates which tissue regions contain signs of toxicity, a tissue visualization may be created using the steps described with respect to FIG. 5. The user may interact with and/or edit the visualization. The user may adjust the visualization so that more tissue is visible (e.g., if they disagree with the result and think an area exhibits toxicity) or less tissue is visible (e.g., if they disagree with the result and think the identified areas do not show toxicity). The user's field of view may be moved to focus upon each region of interest in order of priority, class, or other preferential orders. The user may tag a tissue region with multiple users' differential diagnoses. The outputs and/or visualized regions are logged and/or stored (e.g., to disk, to cloud, to laboratory information system, etc.).

Exemplary Prediction of Parasitic Infestations Tool: According to one embodiment, a method includes a visualization of AI detection of parasites in whole slide images. Pathologists may be called upon to diagnose parasitic infections, e.g., protozoan and helm inthic caused disease. For example, diagnosis of *Naegleria fowleri* (commonly referred to as "brain-eating amoeba") may be diagnosed through pathologic examination of brain tissue. Using an AI that produces a salient region overlay M that indicates which tissue regions contain signs of parasitic infection, a tissue visualization may be created using the steps described with respect to FIG. 5. The user may interact with and/or edit the visualization. The user may adjust the visualization so that more tissue is visible (e.g., if they disagree with the result) or less tissue is visible (e.g., if they disagree with the result and think the identified areas are not a parasitic infection). The user's field of view may be moved to focus upon each region of interest in order of priority, class, or other preferential orders. The user may tag a tissue region with multiple user's differential diagnoses. The outputs and/or visualized regions may be logged and/or stored (e.g., disk, cloud, laboratory information system, etc.).

Exemplary Biomarkers Tool: According to one embodiment, a method includes using AI to characterize and/or identify different biomarkers. In cancer pathology, one task of a pathologist is to characterize and/or identify different biomarkers, with additional testing (e.g., immunohistochemistry, sequencing, etc.). These may apply to all tissue types (e.g., HER2 for lung, breast, colon). Using an AI that produces a salient region overlay M that indicates which tissue regions contain invasive cancer, a tissue visualization may be created using the steps described with respect to FIG. 5. The user may customize what the tissue visualization shows based on definitions for the target output. For example, some users might prefer to see all present biomarkers, whereas others might only want to see present biomarkers with clinically actionable steps available (e.g., drug or treatment pathway). The user's field of view may be moved to focus upon each region of interest in order of priority, class, or other preferential orders. The outputs and/or visualized regions are logged as part of the case history within the clinical reporting system. The user may tag a tissue region with multiple user's differential diagnoses.

Figure 7:
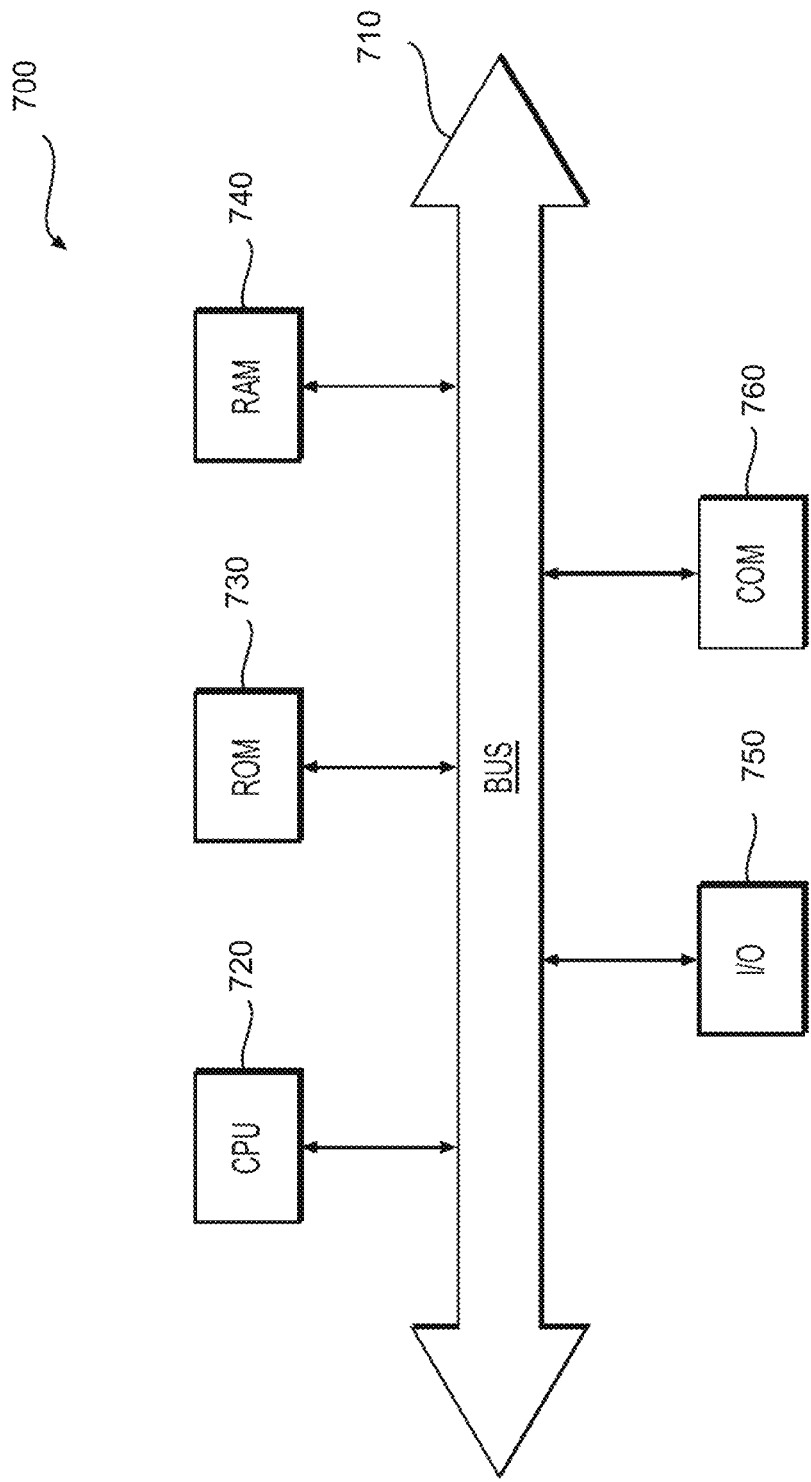
FIG. 7 depicts an example system that may execute techniques presented herein.

FIG. 7 depicts an example device 700 that may execute techniques presented herein. Alternatively, a plurality of devices 700 may execute techniques presented herein. Device 700 may include a central processing unit (CPU) 720. CPU 720 may be any type of processor device including, for example, any type of special purpose or a general-purpose microprocessor device. As will be appreciated by persons skilled in the relevant art, CPU 720 also may be a single processor in a multi-core/multiprocessor system, such system operating alone, or in a cluster of computing devices operating in a cluster or server farm. CPU 720 may be connected to a data communication infrastructure 710, for example, a bus, message queue, network, or multi-core message-passing scheme.

Device 700 also may include a main memory 740, for example, random access memory (RAM), and also may include a secondary memory 730. Secondary memory 730, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 730 may include other similar means for allowing computer programs or other instructions to be loaded into device 700. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 700.

Device 700 also may include a communications interface ("COM") 760. Communications interface 760 allows software and data to be transferred between device 700 and external devices. Communications interface 760 may include a modem, a network interface (such as an Ethernet card), a communications port, a PCMCIA slot and card, or the like. Software and data transferred via communications interface 760 may be in the form of signals, which may be electronic, electromagnetic, optical, or other signals capable of being received by communications interface 760. These signals may be provided to communications interface 760 via a communications path of device 700, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 700 also may include input and output ports 750 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and modules may be implemented in software, hardware, or a combination of software and hardware.

The tools, modules, and functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples be considered as exemplary only.

What is claimed is:
1. A computer-implemented method for analyzing an image of a slide corresponding to a pathology specimen, the method comprising:
determining, using an artificial intelligence (AI) system, a salient region overlay for at least one digitized image of the pathology specimen;

representing the salient region overlay by a set of super-pixels associated with a score;
suppressing, based on a diagnostic value for each pixel, one or more non-salient regions of the at least one digitized image; and
normalizing the salient region overlay to obtain a variable, the salient region overlay represented by a binary segmentation of the at least one digitized image indicating if each pixel has a salient feature present.

2. The computer-implemented method of claim 1, further comprising converting the salient region overlay into a tissue map.

3. The computer-implemented method of claim 1, further comprising:
detecting the salient feature using the AI system on the at least one digitized image to produce a tissue visualization.

4. The computer-implemented method of claim 1, wherein the at least one digitized image comprises related case information, patient information and information from a clinical system.

5. The computer-implemented method of claim 1, further comprising alerting a user when the salient region overlay is available.

6. The computer-implemented method of claim 1, further comprising resizing the salient region overlay to a same size as the at least one digitized image.

7. The computer-implemented method of claim 1, further comprising:
indicating, by the AI system, a diagnostic value for each pixel.

8. The computer-implemented method of claim 1, further comprising representing the salient region overlay by a semantic segmentation of the at least one digitized image indicating a score or probability for each pixel.

9. A system for analyzing an image of a slide corresponding to a pathology specimen, the system comprising:
at least one memory storing instructions; and
at least one processor configured to execute the instructions to perform operations comprising:
determining, using an artificial intelligence (AI) system, a salient region overlay for at least one digitized image of the pathology specimen;
representing the salient region overlay by a set of super-pixels associated with a score;
suppressing, based on a diagnostic value for each pixel, one or more non-salient regions of the at least one digitized image; and
normalizing the salient region overlay to obtain a variable, the salient region overlay represented by a binary segmentation of the at least one digitized image indicating if each pixel has a salient feature present.

10. The system of claim 9, the operations further comprising:
converting the salient region overlay into a tissue map.

11. The system of claim 9, the operations further comprising:
detecting the salient feature using machine learning on the at least one digitized image to produce a tissue visualization.

12. The system of claim 9, the operations further comprising developing a pipeline to archive prospective patient data.

13. The system of claim 9, the operations further comprising representing the salient region overlay by a semantic segmentation of the at least one digitized image indicating a score or probability for each pixel.

14. A computer-implemented method for analyzing an image of a slide corresponding to a pathology specimen, the method comprising:
determining, using an artificial intelligence (AI) system, a salient region overlay for at least one digitized image of the pathology specimen;
suppressing, based on a diagnostic value for each pixel, one or more non-salient regions of the at least one digitized image;
normalizing the salient region overlay to obtain a variable, the salient region overlay represented by a binary segmentation of the at least one digitized image indicating if each pixel has a salient feature present; and
representing the salient region overlay by a semantic segmentation of the at least one digitized image indicating a score or probability for each pixel.

15. The computer-implemented method of of claim 14, further comprising converting the salient region overlay into a tissue map.

16. The computer-implemented method of of claim 14, further comprising: detecting the salient feature using the AI system on the at least one digitized image to produce a tissue visualization.

17. The computer-implemented method of of claim 14, further comprising: resizing the salient region overlay to a same size as the at least one digitized image.

18. The computer-implemented method of of claim 14, further comprising: indicating, by the AI system, a diagnostic value for each pixel.

19. A system for analyzing an image of a slide corresponding to a pathology specimen, the system comprising:
at least one memory storing instructions; and
at least one processor configured to execute the instructions to perform operations comprising:
determining, using an artificial intelligence (AI) system, a salient region overlay for at least one digitized image of the pathology specimen;
suppressing, based on a diagnostic value for each pixel, one or more non-salient regions of the at least one digitized image;
normalizing the salient region overlay to obtain a variable, the salient region overlay represented by a binary segmentation of the at least one digitized image indicating if each pixel has a salient feature present; and
representing the salient region overlay by a semantic segmentation of the at least one digitized image indicating a score or probability for each pixel.

20. The system of claim 19, further comprising representing the salient region overlay by a set of super-pixels associated with a score or a probability for the salient feature being present or absent.

* * * * *